United States Patent [19]

Dennis

[11] Patent Number: 4,493,420

[45] Date of Patent: Jan. 15, 1985

[54] METHOD AND APPARATUS FOR DETECTING BOUNDED REGIONS OF IMAGES, AND METHOD AND APPARATUS FOR SORTING ARTICLES AND DETECTING FLAWS

[75] Inventor: Timothy J. Dennis, Colchester, England

[73] Assignee: Lockwood Graders (U.K.) Limited, United Kingdom

[21] Appl. No.: 343,574

[22] Filed: Jan. 28, 1982

[30] Foreign Application Priority Data

Jan. 29, 1981 [GB] United Kingdom ................. 8102752

[51] Int. Cl.³ .......................... B07C 5/34; H04N 7/18
[52] U.S. Cl. .................................... 209/587; 209/701; 209/939; 358/106; 382/45
[58] Field of Search .............................. 209/576–578, 209/580, 581, 585, 587, 701, 939; 356/237, 425, 426, 445; 358/101, 106, 107, 515; 364/555; 382/44, 45

[56] References Cited

U.S. PATENT DOCUMENTS

| | | | |
|---|---|---|---|
| 3,887,762 | 6/1975 | Uno et al. | 358/106 |
| 3,963,866 | 6/1976 | Tanie | 358/107 X |
| 3,976,982 | 8/1976 | Eiselen | 382/44 |
| 4,122,951 | 10/1978 | Alaminos . | |
| 4,163,991 | 8/1979 | Burrig | 358/106 X |
| 4,186,836 | 2/1980 | Wassmer et al. . | |
| 4,242,702 | 12/1980 | Kuni et al. | 358/106 |
| 4,319,269 | 3/1982 | Kajiura et al. | 358/106 |
| 4,327,375 | 4/1982 | Leclerc | 358/106 X |
| 4,348,277 | 9/1982 | Cowlin et al. . | |
| 4,351,437 | 9/1982 | Long | 209/939 X |
| 4,403,294 | 9/1983 | Hamada et al. | 358/106 X |
| 4,424,530 | 1/1984 | Taylor | 358/106 X |

FOREIGN PATENT DOCUMENTS 0018861 11/1980 European Pat. Off. .
2430272 2/1980 France .

OTHER PUBLICATIONS

"Control Engineering", vol. 6, No. 1, p. 77, (Jan. 1969).
"Digital Picture Processing", Rosenfeld et al., pp. 272–369, (1976).

Primary Examiner—David A. Scherbel
Assistant Examiner—Edward M. Wacyra
Attorney, Agent, or Firm—Cushman, Darby & Cushman

[57] ABSTRACT

Image processing apparatus for detecting a bounded region of an image includes a scanning device such as a T.V. camera, to scan the image via a raster scan to produce a signal indicative of image intensity at a plurality of picture points and comparators to compare the image intensity at each of the picture points with that of a neighboring point in each of at least two directions to derive therefrom a difference value and thereby detect a positive-going or negative-going boundary. Picture points are labelled as corresponding to region boundaries whenever the difference values exceed a predetermined threshold value. The region boundaries are then expanded by labelling further picture points as region boundaries. All boundaries in a particular direction are expanded in the same direction irrespective of whether they are negative-going or positive-going. Thus, boundaries between neighboring picture elements along the scan line are expanded to successive neighboring picture elements along the scan line and boundaries between neighboring picture elements on neighboring scan lines are expanded to neighboring successive scan lines. The expanded boundaries are then subjected to a time-shift to superimpose the expanded boundaries for a region lying wholly within a bounded region of the image.

19 Claims, 18 Drawing Figures

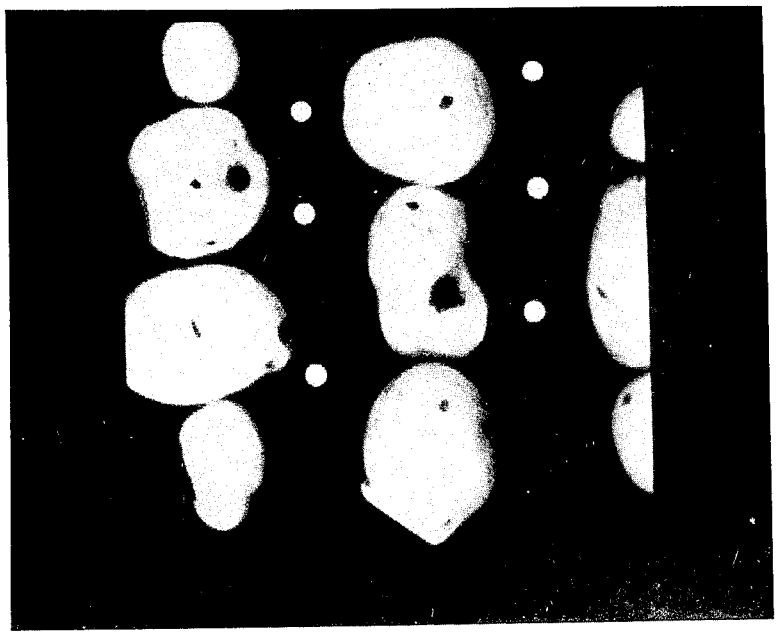
→ FIG. 5.
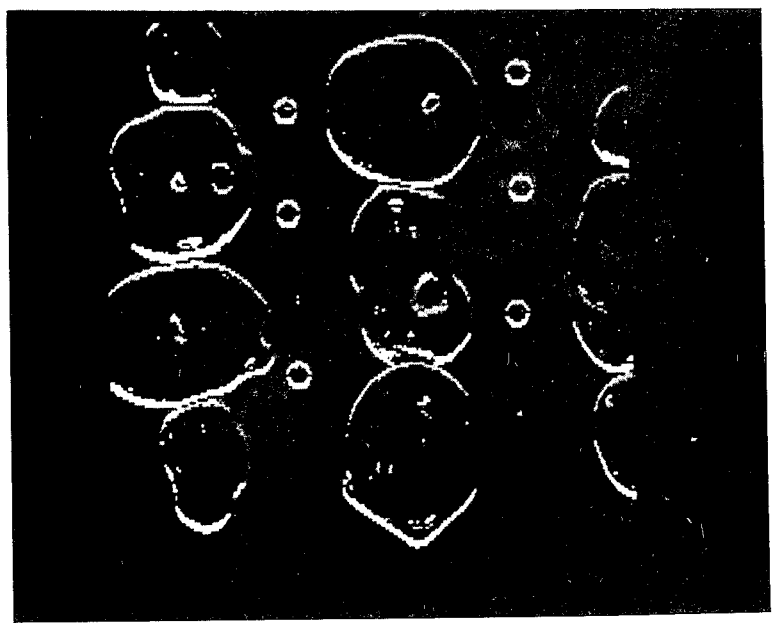
→ FIG. 6.

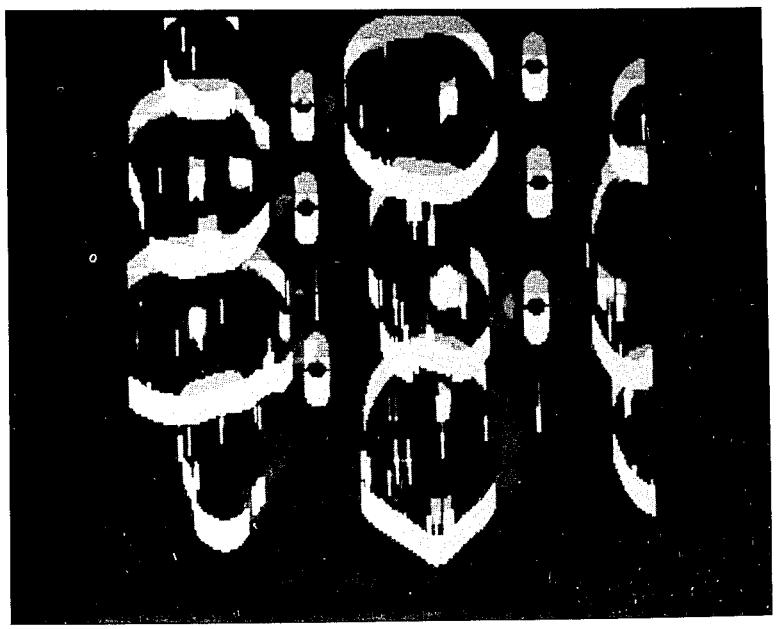
→ FIG. 7.
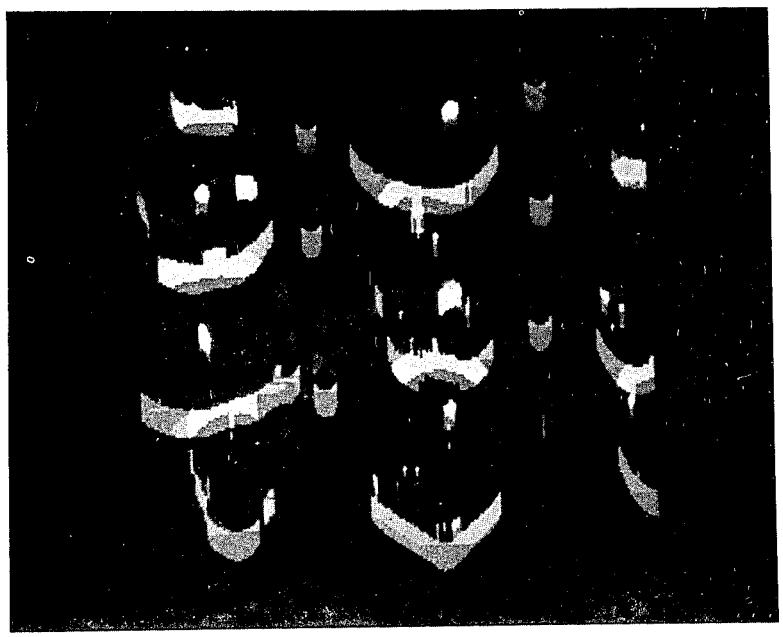
→ FIG. 8.

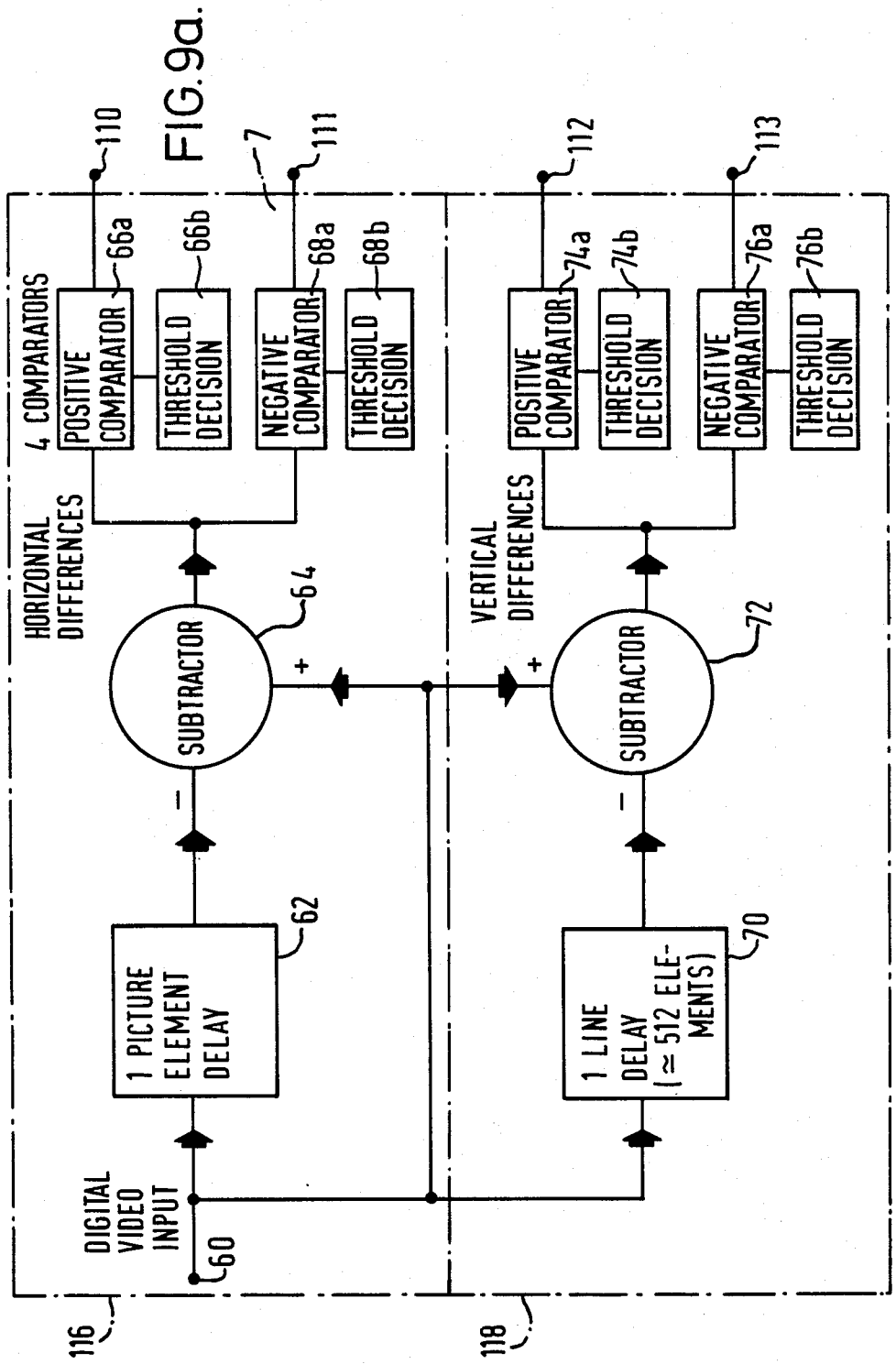

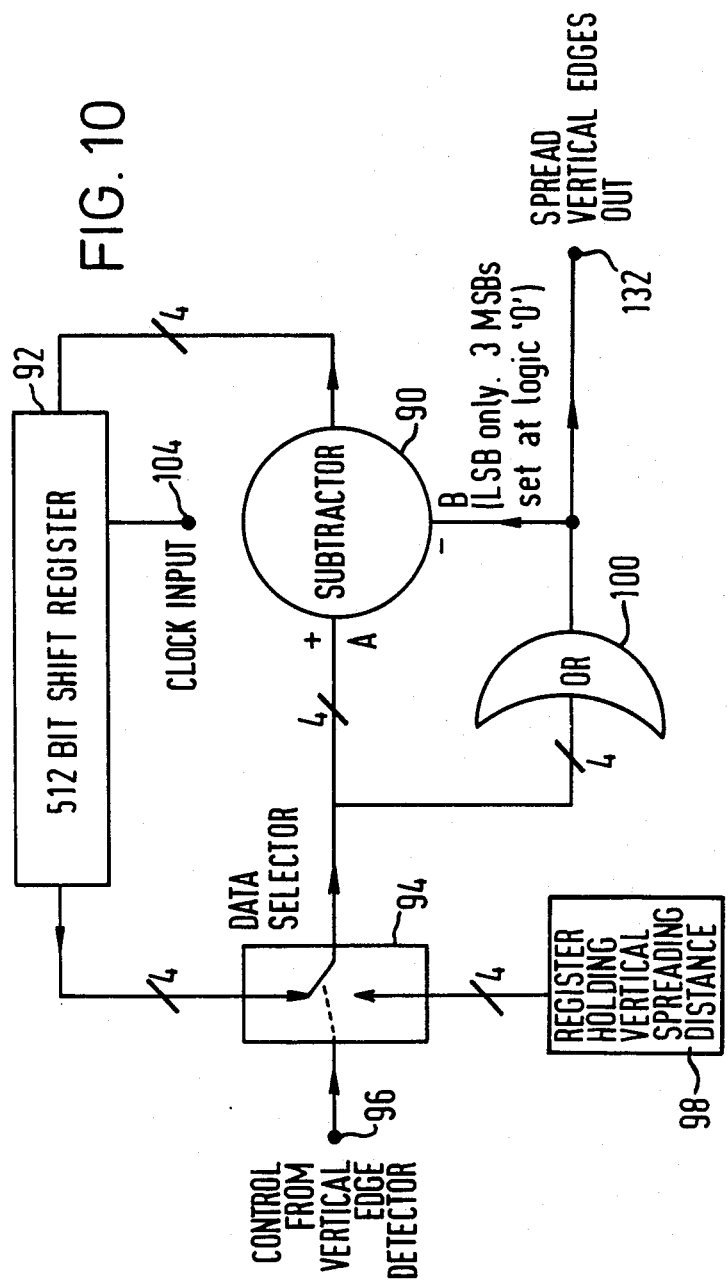

All 4 edges overlap in the central square (B-W) Horiz.
(B-W) Vert.
(W-B) Vert.
(W-B) Horiz.

Origional Position of Black Area

METHOD AND APPARATUS FOR DETECTING BOUNDED REGIONS OF IMAGES, AND METHOD AND APPARATUS FOR SORTING ARTICLES AND DETECTING FLAWS

BACKGROUND AND SUMMARY OF THE INVENTION

This invention relates in one aspect to an apparatus and a method for the sorting of articles in which the sorting is carried out in dependence on the presence of a surface feature of the article having a value of reflectivity substantially different from a reference value. This aspect of the invention has particular but not exclusive application to the inspection of root vegetables during processing, for example newly-peeled potatoes.

A further aspect of the invention relates to a method and apparatus for processing image data to determine the presence of bounded regions therein. The image processing method is particularly suitable for use in the foregoing sorting metod and may also be useful for detecting flaws in sheet material such as laminated plastics, or, for example in paintwork.

It is particularly important that sub-standard potatoes, particularly those displaying large black spots, should be excluded from further processing operations such as chipping or canning subsequent to peeling. The inspection procedure now commonly employed relies on operators picking out defective potatoes by hand as they pass along an inspection table. Such a procedure is difficult and inefficient however since potatoes newly peeled by a steam process are hot and slippery. In co-pending patent application No. 7938336 the present Applicant has proposed a semi-automatic inspection procedure in which in one form the inspection area of a conveyor is viewed by means of a television camera and an operator indicates the coordinates of a defective potato in a T.V. monitor picture by touching the screen with a light pen. The contact position is sensed and the information is used to determine the time of arrival of the defective potato at the end of the conveyor. It can then be arranged that a selection device will operate to divert the path of the defective potato from the main stream when it reaches the end of the conveyor. Such selection devices for example in the form of an array of pneumatically deflectable fingers each independently controlling a small part of the width of the conveyor are well known.

It is an object of the present invention at least in preferred embodiments thereof to avoid the need for a supervisory operator and to provide completely automatic means for processing an image signal to determine the position of a defect or desired feature and to convey an appropriate instruction to the selection device.

In accordance with the first aspect of the invention there is provided apparatus for detecting the presence in an article or articles having predominantly a first value of reflectivity of regions having a second value of reflectivity substantially different from that of the first value, which apparatus comprises means for scanning the article or articles to produce an image signal, and means for processing the image signal, to produce an output when the image signal indicates a surface feature in the scanned region having the said second value of reflectivity, whenever such feature lies wholly within an area having the first value of reflectivity.

It should be appreciated that the reflectivities of areas having "first" or "second" reflectivity values need not be uniform over the whole of the said areas, and allocation of a picture point to "first" or "second" reflectivity values may be carried out simply according to whether the reflectivity is greater or less than an arbitrary value. However it is greatly preferred that the distinction between "first" and "second" reflectively values should be made by labelling picture points of the image as corresponding to a boundary between the said first and second regions when local difference values between neighbouring picture points is greater than a specified threshold, and labelling as points of the "second" reflectivity value only those surrounded on all sides by such a boundary.

This aspect of the invention is thus particularly suitable for use where boundaries between regions are reasonably sharply defined.

In accordance with a preferred embodiment of this first aspect of the invention there is provided article sorting apparatus comprising conveying means for conveying through an inspection region articles having predominantly a first value of surface reflectivity but bearing occasional surface features having a second value of reflectivity which is substantially different from the first value, means for illuminating each article in the inspection region, sensing means responsive to reflected radiation reflected from the articles for scanning the inspection region to derive an image signal, means for processing the image signal to detect the presence of and to indicate the location of a surface feature having the second value of reflectivity whenever such feature lies, as viewed by the sensing means, wholly within an area having the first value of reflectivity, and deflection means responsive to such detection and indication of location to cause the article bearing such feature to be routed differently from the other articles.

In accordance with a second aspect of this invention, there is provided apparatus for detecting a bounded region of an image, which apparatus comprises means for scanning the image to produce a signal indicative of intensity at a plurality of picture points, means for deriving difference values between neighbouring points in a plurality of directions to determine the presence of region boundaries, and means for labelling a picture point as lying within a bounded region according to whether or not it is surrounded, for example surrounded on four sides, by such region boundaries. The apparatus preferably includes means for labelling additional picture points, for example labelling them as being region boundaries, according to whether or not they lie within a predetermined number of picture points in a specified direction of a region boundary, and means for thereby determining which of the said picture points lie within a predetermined number of picture points of boundaries in each of the said plurality of directions, and therefore correspond to picture points lying within a bounded region.

In a preferred embodiment, the image processing apparatus comprises apparatus for detecting a bounded region of an image, which apparatus comprises means for scanning the image via a raster scan to produce a signal indicative of image intensity at a plurality of picture points, means for comparing the image intensity at each of the said picture points with that of a neighbouring point in each of at least two directions to derive therefrom a difference value, means for labelling the picture points as corresponding to region boundaries whenever the difference values exceed a predetermined threshold value, means for expanding the region boundaries by labelling further picture points as region boundaries such that boundaries between neighbouring picture elements along a scan line are expanded to successive neighbouring picture elements along the said scan line and boundaries between neighbouring picture elements or neighbouring scan lines are expanded to neighbouring successive scan lines, and means for delaying signals associated with different types of region boundaries by different amounts to superimpose those signals corresponding to picture points labelled as being included within a plurality of expanded boundaries.

The means for processing the image signal may include storage means for storing digitally the value of the signal for each of an array of points and means for deriving difference values between neighbouring points in a plurality of directions to determine the presence of a closed boundary between an outer area corresponding to the first value of reflectivity and an inner area corresponding to the second value of reflectivity.

The term "neighbouring points" as used herein is intended to include not only adjacent points in any particular direction but also points spaced from the point of interest by, for example one or two picture points in the direction of interest. Difference values derived from every alternate point have been found to produce effective boundary determinations.

The means for processing the image signal may further include means for reallocating difference values representing the closed boundary to points within the boundary to produce by superimposition a localised area of enhanced value and means for determining the location of the area of enhanced value.

The means for processing the image signal may further include means for reallocating difference values representing a boundary which encloses an area corresponding to the first value of reflectivity to points outside that boundary such that the boundary is represented by points of reduced value.

The means for processing the image signal may further include means for deleting from the storage means all difference values below a predetermined threshold value such that the area of enhanced value is substantially isolated.

The processing means conveniently is formed by electronic circuitry, which may be specialised circuitry costructed for the purpose, or may consist of a microprocessor or other general purpose computer programmed to carry out the various functions set out in the preceding paragraphs, and in the remainder of the specification. In this connection it is to be appreciated that where, for example, the processing means comprises a microprocessor, it is usual that many parts of the microprocessor will be utilised at various times in operation to carry out more than one function required in accordance with the invention. Thus it is not necessarily the case that any particular function required in accordance with the invention is allocated to any particular operating means within a computer, but rather that there should merely be provided appropriate means for carrying out the function, and at other times that means may carry out other functions.

It will be apparent that when a desired feature has been located within the scanning area, and thence within the inspection region, the article bearing such feature may be tracked along the conveying means by deriving a speed dependent signal (e.g. from the conveying means drive mechanism) so that the deflection means may be operated at the appropriate instant.

The scanning pattern may consist of a conventional television type of raster, and may be directed along the direction of movement so that the position of the article in the width of the conveyor may be derived from the frame timing of the pattern. In the direction of movement the position of the article may be identified by reference to the interception of the line scan by regularly occurring structural features on the conveying means. Alternatively the raster scan may be perpendicular to the direction of movement, in which case these are reversed.

The sensing means may be a television camera which may be operated under continuous lighting if the conveying means proceeds in a stepwise or batch inspection manner. If the conveying means provides continuous movement strobe illumination synchronised with the frame frequency may be advantageous in certain circumstances, the imaging signal being extracted only in one frame in each sequence of three or four frames.

Where the articles are rounded articles such as potatoes, the conveying means preferably comprises a roller table over which the articles are conveyed in the inspection area. A roller table is a conveyor formed of a plurality of rotatable elongate members, known as rollers, connected together by, for example, side chains to form an endless array in which the rollers are spaced apart with their axes parallel and transverse to the direction of translational movement. Articles are conveyed in transversely extending rows supported by adjacent pairs of rollers. The rollers are rotated over at least part of the endless conveyor path in order to rotate the articles conveyed thereon to evenly distribute the articles on the conveyor and to sequentially present the whole surface of the articles for inspection. The rollers and the spaces between them may be such as to be sensed by the sensing means as having a reflectivity close to the second value.

In the inspection of peeled potatoes the feature to be searched for is a blackened area on the otherwise white surface for which purpose the rollers and background are preferably also black. The rollers may be marked to provide a video reference to their position and therefore to the probable position of potatoes between the rollers whereby signals purporting to relate to the presence of a potato in a different position may be rejected. Preferably however, a video reference signal for controlling the timing of the operation of the deflection means is produced by the mechanism moving the roller bed.

Preferably the speed of the conveying means for potatoes is so controlled with respect to the rate of loading that the rollers are sufficiently occupied to prevent a potato which has been identified as defective from moving across the width of the roller away from its determined location. Such movement would cause the selection mechanism to be operated incorrectly.

The deflection means may comprise a bank of fingers arranged to occupy the whole width of the conveying means and at a level such that articles leaving the conveyor must pass or be deflected by one or more of the fingers. Appropriate fingers are operable independently or in groups in response to signals from the image signal processing means and from the conveying means to select for direction in a predetermined path an article previously identified in the inspection region.

It is particularly preferred that an output of the processing means is arranged to actuate the deflector means in dependence upon first and second co-ordinate signals representative of first and second orthogonal co-ordinates of a location in the scanned area, the orthogonal co-ordinates being arranged with the first co-ordinate in a direction corresponding to a direction across the path of travel of the conveyor means at the inspection area and with the second co-ordinate in a direction corresponding to a direction aligned along the path of travel of the conveyor means at the inspection area. It is further preferred that the deflector means comprises an array of deflector devices arranged across the path of the conveyor means downstream of the inspection area, and drive means for driving selected deflector devices, the selection of deflector devices actuated being controlled in dependence upon the said first co-ordinate signals and the timing of operation of the deflector devices being controlled in dependence upon the said second co-ordinate signals.

The deflector means may comprise fingers for deflecting articles falling from the conveyor means, the fingers being actuable between two or more positions so as to direct the falling articles onto different conveyor belts or other receptacles. In the case of potatoes or other root vegetables or bulbs, the said fingers can be of a kind well known in themselves for separating produce from soils and stones using, for example, x-ray beams to distinguish the difference. Usually the deflector means will be located downstream of the inspection area, and in such cases the signals controlling actuation of the deflector means will be processed in control means in order to compensate for the time delay for the articles to pass from the indicated transient positions in the inspection area to the deflector means.

However it is to be appreciated that the deflector means may constitute means for deflecting selected, or unselected articles at substantially the same time that the articles are selected. In such case of course no time delay needs to be introduced which is related to the speed of conveying. One method of achieving such deflection is for example to provide beneath the conveyor means a bank of ejector rods which can be triggered to project upwardly through apertures in the conveyor means to strike, for example, unwanted articles and to propel such articles clear of the conveyor means. Such arrangements have previously been used in connection with sorting of potatoes from stones, where unwanted stones have been ejected in this manner. It is to be understood that the term deflector means includes not only means for deflecting articles through differing angles during travel of the articles, but also includes means for removing articles entirely from a conveying path, and indeed includes any means for effecting sorting of objects in response to the signals generated by the processing means.

In accordance with another aspect of the invention there is provided a method of sorting articles by selecting from a plurality of articles having a first value of surface reflectivity articles bearing a surface feature having a second value of reflectivity which is substantially different from the first value, the method comprising the operations of conveying such articles through an inspection region, illuminating each article in the inspection region, scanning the inspection region by sensing means responsive to reflected radiation reflected from the articles to derive an image signal, processing the image signal to detect the presence of and to indicate the location of a surface feature having the second value of reflectivity whenever such feature lies, as viewed by the sensing means, wholly within an area having the first value of reflectivity, and operating deflection means responsive to such detection and indication of location to cause the article bearing such feature to be deflected from the other articles.

In accordance with a further aspect of the invention, there is provided a method of detecting a bounded region of an image, which method comprises scanning the image to produce a signal indicative of intensity at a plurality of picture points, deriving difference values between neighbouring points in a plurality of directions to determine the presence of region boundaries, and labelling a picture point as lying within a bounded region according to whether or not it is surrounded on four sides by such region boundaries.

Preferably, additional picture points are labelled as corresponding to region boundaries according to whether or not they lie within a predetermined number of picture points in a specified direction of a region boundary, and thereby it is determined which of the said picture points lie within a predetermined number of picture points from boundaries in each of the said plurality of directions, and therefore correspond to picture points lying within a bounded region.

In accordance with yet a further aspect of the invention, there is provided a method of detecting a bounded region of an image, which method comprises scanning the image via a raster scan to produce a signal indicative of image intensity at a plurality of picture points, comparing the image intensity at each of the said picture points with that of a neighbouring point in each of at least two directions to derive therefrom a difference value, labelling the picture points as corresponding to region boundaries whenever the difference values exceed a predetermined threshold value, expanding the region boundaries by labelling further picture points such that boundaries between neighbouring picture elements along a scan line are expanded to successive neighbouring picture elements along the said scan line and boundaries between neighbouring picture elements on neighbouring scan lines are expanded to neighbouring successive scan lines, delaying signals associated with different types of region boundaries by different amounts to superimpose those signals corresponding to picture points labelled as being included within a plurality of expanded boundaries.

BRIEF DESCRIPTION OF THE ACCOMPANYING DRAWING

An embodiment of the invention will now be described by way of example with reference to the accompanying drawings in which.

Figure 9:
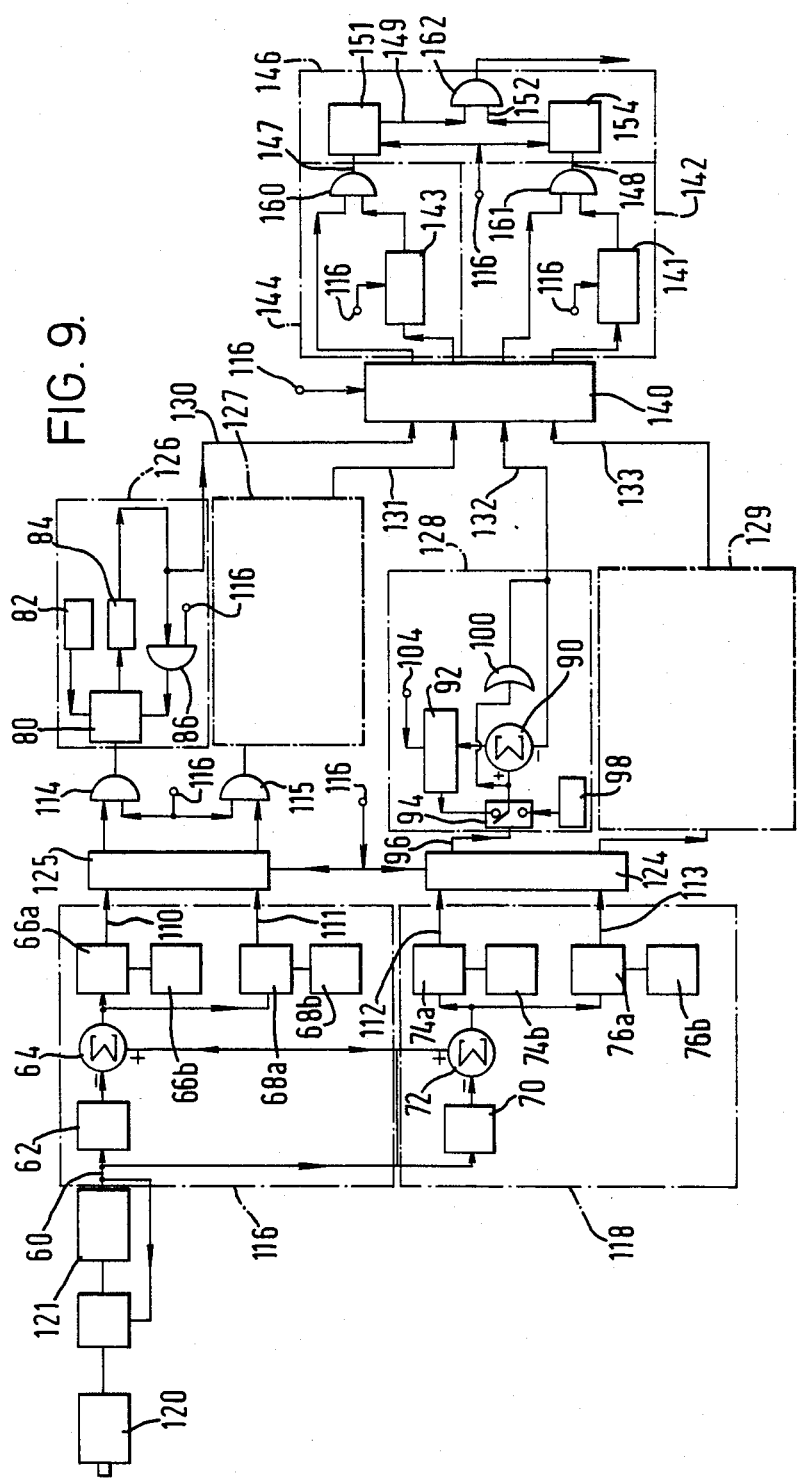
Figure 9B:
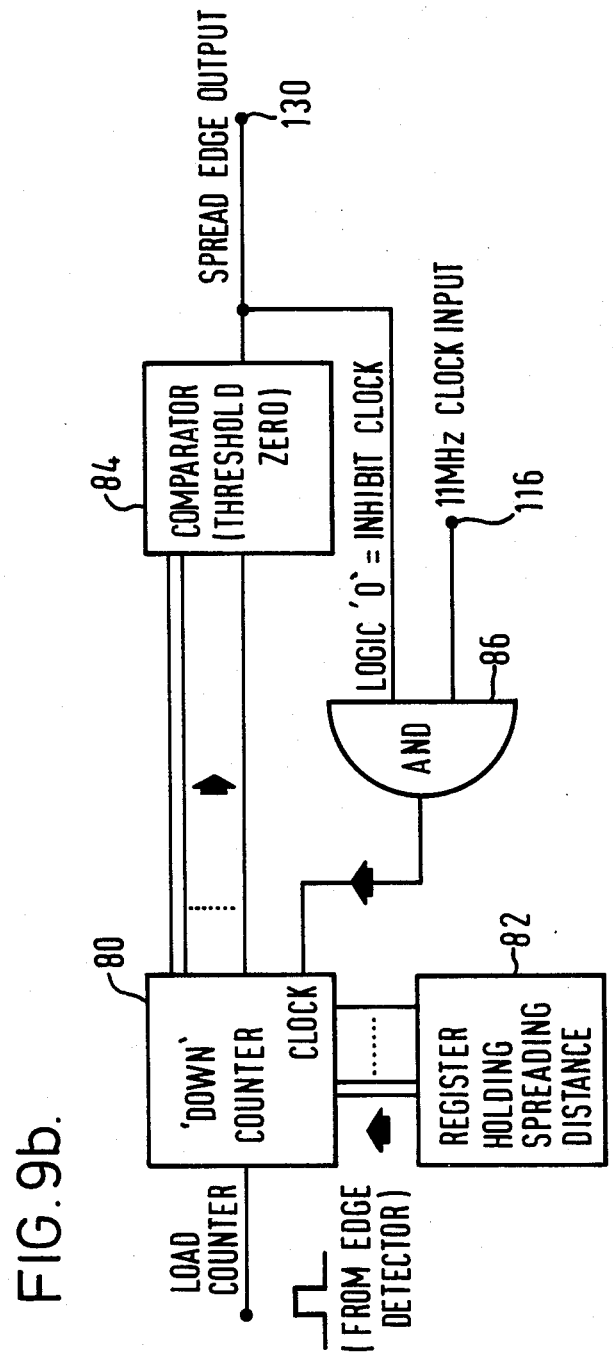

FIGS. 3(a), 3(b), 3(c) and FIG. 4 illustrate aspects of the method of image processing according to the invention;

FIGS. 5 to 8 represent in outline form successive steps in the processing of a static image;

FIG. 9 is a schematic circuit diagram of image processing apparatus according to the invention;

FIGS. 9(a) 9(b) and 10 represent schematically various points of FIG. 9 in more detail; and FIGS. 11(a)–11(d) represent schematically various stages in bringing the spread edges into register.

DETAILED DESCRIPTION OF THE PREFERRED EXEMPLARY EMBODIMENTS

In order to assist in the putting into effect of the present invention, reference is made to the following documents which disclose various known techniques of relevance to the present invention.

In commonly owned U.S. Pat. Nos. 4,351,437 and 4,348,277 there are described various items of hardware such as a roller table, and various techniques for operating such hardware such as methods of operating a bank of deflecting devices. In a published book entitled Digital Picture Processing by Rosenfeld and Kak, published by Academic Press, New York 1976, there is described for example at pages 274 to 369 a technique for signal processing which is related to the processing technique to be described herein.

Figures 1, 3A:
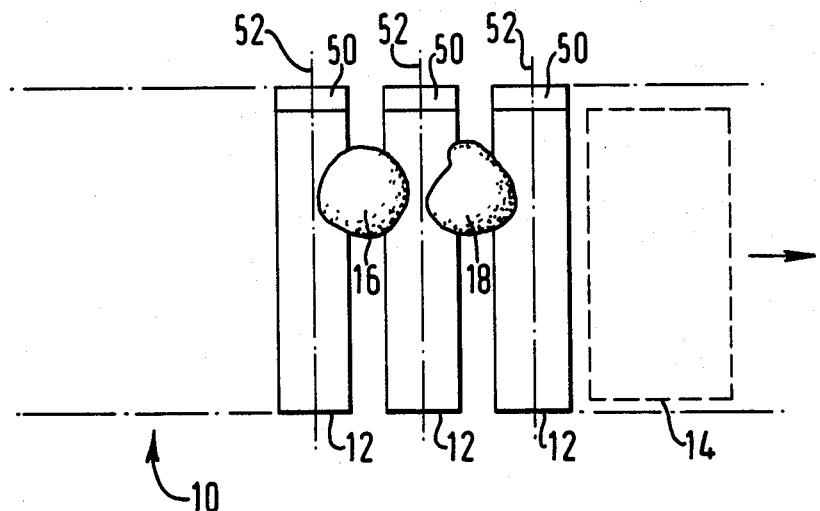
FIG. 1 represents in plan view a roller table for the inspection of potatoes.

Referring now to FIG. 1, a conveyor 10 seen in plan view comprises a table formed of rollers 12 which in known manner are carried round a loop path by a transport mechanism such as a chain (not shown). The path includes an inspection region generally indicated as an area enclosed by a broken line 14 through which the rollers 12 are considered as moving from left to right. The rollers are also caused to rotate at least during their passage through the inspection region. Peeled potatoes 16, 18 are shown as having been conveyed to the inspection region from a loading position (not shown) at the extreme left-hand end of the roller table. The diameter of the rollers and the gap between them is arranged so that a potato within the acceptable range of size will travel for the whole length of the conveyor between a single pair of rollers and will usually lie between the centre lines of those rollers. Thus contact between the potatoes in adjacent gaps is unlikely and the time of travel of a potato along the conveyor is exactly indicated by the speed of the conveyor.

Figure 2:
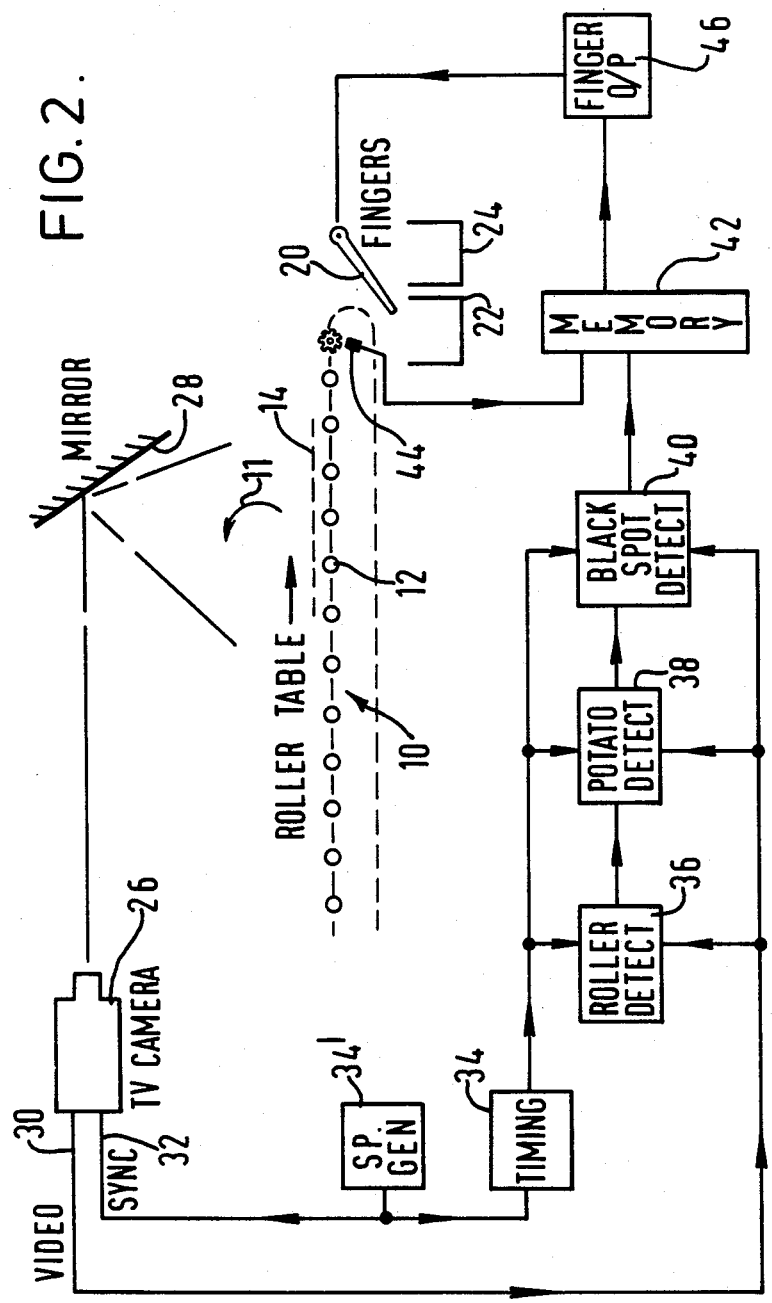
FIG. 2 represents schematically article sorting apparatus embodying the invention and incorporating the table of FIG. 1.
Figure 4:
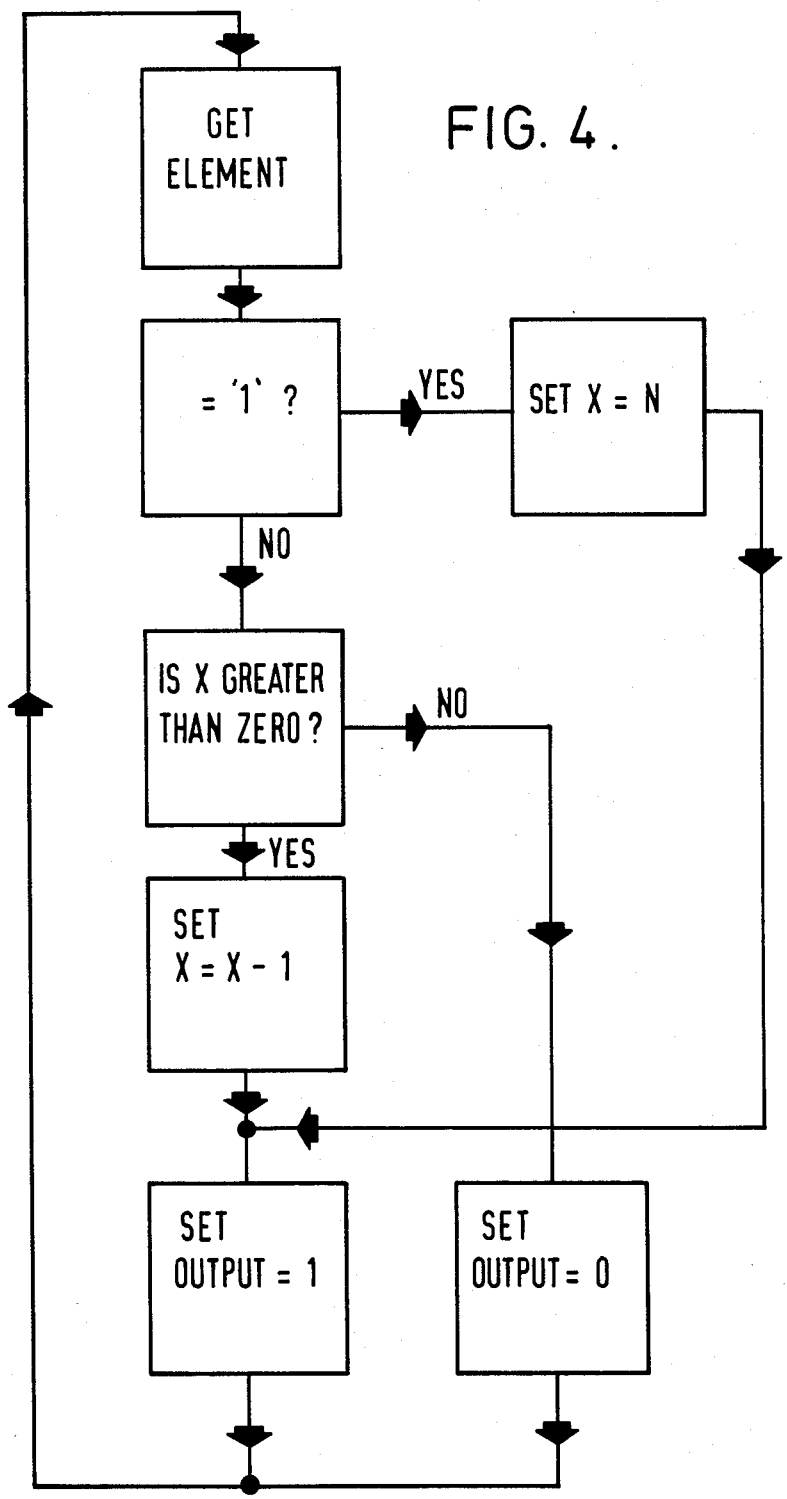

The further operation of the system is indicated in the diagrammatic side view of the conveyor in FIG. 2. At the right-hand end of the conveyor, that is at the end of the loop, potatoes fall off the rollers 12 onto a bank of fingers 20 which can be positioned pneumatically either to deflect the good quality potatoes into an ACCEPT bin 22 or to allow those identified during inspection as being defective to fall into a REJECT bin 24.

The inspection region 14 is observed by means of a T.V. camera 26 by reflection from a plane mirror 28 mounted above the conveyor 10. The camera circuits provide a video output signal on a line 30 and a scan synchronising signal on a line 32 for processing in a computer comprising units 34 to 42. Data on the location of defective potatoes is held in memory 42 for co-ordination with a conveyor speed signal from a pick-up point 44 to provide an output signal to a finger control unit 46.

The direction of line scan in camera 26 may be along or perpendicular to the direction of motion of the roller table, that is at right angles or parallel to the rollers themselves. The former orientation enables the position of a potato across the width of the roller table to be determined as a proportion of a frame scan period which is much larger than a line scan period and therefore easier to measure. The rollers may then themselves provide indicia of position longitudinally. For this purpose, each roller may be coated with black plastics material or otherwise darkened to provide good contrast with the whiteness of the potato, and one end of each roller (indicated at 50 in FIG. 1) may be whitened. Positional reference signals may therefore be obtained at the beginning of each frame and sensed in the synchronisation signal by a "roller detect" unit 36 of the computer. Similar signals marking a transition from black to white will generally indicate the presence of a potato. Such signals can be monitored for validity by reference to the roller positional signals since a potato must almost certainly lie between the centre lines of adjacent rollers as indicated at 52 in FIG. 1.

In a preferred arrangement, however, the scan direction is perpendicular to the direction of motion, and positional reference signals are derived directly from the mechanism moving the roller bed.

A verified signal is then accepted by a "potato detect" unit 38 (strictly speaking a boundary or edge detection unit, in the embodiment hereinafter described). Confirmation of the presence of an edge means that any immediately subsequent transition from white to black may represent a defect in the potato. This is not immediately certain however since the scan line may have crossed a narrow segment of a potato and a next black signal may again represent background. This event does not lead to a false output signal because the part of the computer indicated by a "black spot detect" unit 40 is programmed to compare the image data at a matrix of picture points. As will be explained later a defect signal is only produced at the output of unit 40 if the black area detected is completely bounded by white and consequently must then be within a potato. Each of the units 36, 38, 40 operates with reference to timing signals derived by a timing unit 34 from the camera synchronising signal pulse generator $34^1$.

Illumination of the conveyor, by means which are not shown in the drawing, requires the characteristics of the T.V. camera to be considered.

If a T.V. camera is used to reproduce images of moving objects, their motion is bound to obscure detail, whatever the type of camera used. This is due to the fact that any T.V. camera has an effective exposure of 40 ms over which it integrates light falling on its sensitive target. Some cameras, such as vidicons, introduce further degradation owing to an inherently slow time response in the chemical comprising the target.

These factors have not been found significant in practice, but if necessary in any particular application, a mechanical shutter or strobe lights synchronised to the T.V. frame scan may be provided. The latter method is favoured, as it enables the very high light intensity required to be achieved easily at low energy cost and does not require mechanical systems.

Tests have shown that a strobe light can be used to obtain a distortion-free picture of moving objects from a vidicon camera tube provided the picture rate required is somewhat less than normal T.V. frame rates, say 1 in 3 or 1 in 4 normal frames. Only the frame following the strobe flash would be used by the detector, while the effects of lag will have died away before the next. Given the relatively slow speed of the roller table it is found that reduced frame rates of this kind are tolerable.

In addition, it has been found that some reduction in image blurring can be achieved if the rollers rotate in the direction shown by arrow 11, such that the motion of the side of the potatoes facing the camera caused by the rotation of the potato if offset to the overall direction of movement of the potato on the moving rollers.

The signal processing procedure will first be illustrated for simplicity by results obtained from a static image. For this purpose the successive transformations of the original data which are held in the computer store have been read out to a display and photographed. It will be appreciated however that the method and apparatus for signal processing described herein are applicable to a real time inspection system in which it is unnecessary ever to produce a visual image. The problem of detecting black defect spots will first be considered in principle.

The problem is one of pattern recognition subject to particular restrictions. For example, the spots to be detected have widely variable shapes and sizes, so that a technique which performs a template comparison is unsuitable. A further complication is the presence of the black background of the roller table and the consequent need to distinguish between genuine black spots and gaps between potatoes; such a task is straightforward for the human observer, but much less so for a machine.

The method of detecting flawed potatoes which has been developed utilises an image processing method which detects any dark area bounded on all sides by lighter material. The possible problem of spots lying on the edge of a potato as seen by the camera, where they do not appear to have closed boundaries, disappears when it is recalled that during the passage through the inspection region the potatoes are moving and rotated about their long axes by rotation of the rollers. A spot should therefore be completely visible at least once during its passage past the field of view of the camera. The image processing method itself has perfectly general applicability to the detection of bounded regions of an image, at least when such regions have a relatively sharp edge.

The simplest algorithm to locate those picture elements ('pels') which lie within a dark spot is to search in each direction from each spot for a darker to lighter amplitude transition and to label those elements which are surrounded on all sides by such a transition. The range over which the search for a dark/light boundary extends governs the maximum diameter spot which can be detected. FIG. 3(a) illustrates the principle. Elements 0 are dark, elements 1 are light (neglecting for the moment that the input picture actually has a wide contrast range or grey scale). Although the search should proceed in all directions, the horizontal and vertical axes are the most convenient in practice, because of the picture storage format. If the rule is applied to any element in FIG. 3(a), and that element is labelled if a dark-light transition is found within 7 elements in the direction of the search, then all the zeros are correctly identified.

It will be realised that making the search process two-dimensional ensures that the small black areas lying between potatoes (both horizontally and vertically) will not be detected as spots, as they do not constitute a closed curve with transitions within the search distance in both dimensions. There is a possibility of error, however, as is illustrated by a pattern such as that in FIG. 3(b). A diagonal band of zeros (black elements) whilst not a closed black area, would be detected as such by searches within two picture elements in the horizontal and vertical directions. This risk of error could be eliminated by extending the search to 45 degrees to the major axes, but for practical purposes, this has not been found to be necessary.

If the size of the spot is increased as the search distance remains constant, then the number of elements which satisfy the rule falls until a single element, or group of elements, remain at the centre of the area. In general, to give some indication of the presence of a spot with a search distance of N pels, the maximum spot dimensions are $(2N-1)$ pels in both X and Y directions. Between $(2N-1)$ and N pels, the detected area of the spot is less than its actual area. For spots less than N pels in both dimensions, the shape is not affected, all elements lying within it being detected.

The search distance in the X and Y dimensions do not need to be the same: for example, in another application of the principle, it may be necessary to bias the system against particular shapes. Thus, if the search distance is small horizontally and large vertically, the detector will be biased in favour of patterns which are thin horizontally and extended vertically, but will not detect the same patterns rotated through 90 degrees.

The concept of searching for the transitions which surround a black spot has been explained as an aid to the understanding of the process. It is, however, very slow because of the computer time necessary for all the various comparisons required in processing each pel. A method will now be described which is less 'intelligent', but produces the same results in a way which (in the present example) is more efficient in its use of computer time.

The input picture is a sequence of picture elements amplitudes stored in a file as if taken from consecutive columns which run from left to right across the picture. Thus, if there are 100 pels in a column, elements 50 and 150 were horizontally adjacent in the original picture. Element 151 in the file was situated one element to the right of the one element below element 50.

The need to work in two dimensions makes the workspace-storage needs of the processing programs considerable. The range of interest vertically can extend to the full height of the column, as the storage of (say) only 100 pels is required. To obtain the same degree of freedom horizontally requires storage of the whole picture at once, which even if it is as small as 100 by 100 pels, is still excessive. In the software which has been developed, a system of rotating column stores has been used: an area of storage capable of holding around 10 columns of the picture at once is reserved in memory. If the search process is to extend over 10 elements horizontally in the picture, then the first 10 columns of data are read consecutively into the storage area. The eleventh column (when required) goes into the space occupied by the first, the twelfth to the second, and so on. This gives continuous access to the most recent and the nine previously read-in columns of data. It is a simple matter for the software to keep track of any column of interest.

Practical spot-detection is a two stage process; first edges, in horizontal and vertical directions, are identified. Then the map of the edges which results is 'smeared' or spread in a particular way such that the portions denoting edges are expanded, and overlapping smeared regions enable the spots to be located.

The result from the first stage of the process is a version of the picture (in identical storage format to the original) where each element value has been replaced by a 4 bit byte each bit of which indicates whether a particular type of edge was detected as being present at that element.

In the source picture two differences from the current element are calculated: from that above it in the current column and from that to its left in the previous column. Each result is compared with two thresholds.

If the vertical difference is greater than a positive threshold, the presence of a dark to light transition downwards is indicated (the lower edge of a black spot, for example). If the difference is less than a negative threshold the dark and light positions are reversed. Similar possibilities arise from horizontal comparisons. These comparisons enable four different edge types to be identified, shown as the upper row of FIG. 3(c). Identification of just these four edge types has proved sufficient for reasonably reliable spot detection in practice. The lower row of FIG. 3(c) includes four corresponding cases for diagonal edges. The diagonals are represented at 45° but may occur with a wide range of orientation which is only broadly identified by horizontal and vertical differencing. When the dark or light level remains constant the absence of an edge is indicated by a result of zero for each bit. The presence of an edge results in a corresponding bit of the four bit byte being set.

Techniques similar to the second stage spreading process are familiar in pattern recognition work, where they are used frequently to bridge gaps in otherwise continuous areas of binary pictures. Here the technique is somewhat different, in that the desire is to locate regions of the picture where edges of a particular kind lie close together.

In order to do this, when a bit is set in a given byte indicating the presence of a particular edge type, the spreading process sets the corresponding bit for each of a predetermined number of picture point storage locations in a chosen direction to thereby label those picture points as corresponding to region boundaries. In order to locate black spots on a white background, the edge spreading directions must be as follows:
(i) Horizontal Edges (Left to Right)
 a. White to Black: spread to the Right
 b. Black to White: spread to the Left
(ii) Vertical Edges (Downwards)
 a. White to Black: spread Downwards
 b. Black to White: spread Upwards It will be realised that the conditions which would be obtained at a black spot on a white background will result in a region of overlap which indicates the original position of the spot. The region is easy to identify by examining the 4 bit bytes for each element after the spreading, and locating those which consist of all binary 'ones'.

The spreading process is applied independently to each of the four bits of the edge-data byte for each pel. The simplest to consider is the vertical white to black transition which has to be extended downwards. The process is illustrated by the flow-chart of FIG. 4. For each element where there is a '1' (i.e. an edge of the current type of interest), a variable X is set to the constant value N which defines the required extent of the spreading in picture elements. If the next element is not '1' and the variable is greater than zero, the variable is decremented by 1, otherwise it is left at zero. While the variable is greater than zero, the process output is a logic '1', indicating an extended edge.

In the horizontal direction, the technique is similar, but is complicated by the need to maintain an array for the 'X' variables of the flow chart, one for each row of elements.

In the particular program used spreading always works from top to bottom and left to right. To obtain the effect of upward or leftward spreading, signals from different regions of the array are combined.

The steps in the processing of the original image may be seen from FIGS. 5 to 8 which are printed from photographs.

FIG. 5 shows an original picture digitised then read back from the disk to the frame store for display. Its dimensions are 256 elements horizontally (as the signal from the camara had a bandwidth of 5.5 MHz, the sampling rate was 11 MHz) by 200 lines vertically. The two interlaced fields making up the picture are identical, which leads to a rather coarse structure in the vertical direction, since the effective vertical spatial sampling rate is then too low.

The lighting of the potatoes on their rollers was from fluorescent tubes well to the sides of the camera, with their axes at right angles to the rollers to avoid reflections. White spots have been placed on the rollers to demonstrate that the system does respond only to black-on-white defects.

FIG. 5 is the output of the first stage detection process, and shows the raw threshold edge information. The thresholds were set at ±20 quantum levels out of the possible range of ±255. The picture simply reproduces the coded edges as different grey levels. The various levels are allocated as follows:

| Level | Edge Type |
| --- | --- |
| 1 (dark grey) | Horizontal, white-black |
| 2 | Horizontal, black-white |
| 3 | Vertical, white-black |
| 4 (light grey) | Vertical, black-white |

FIG. 7 is the output of the spreading process. It can be seen that the edges of black spots tend to be spread towards each other while white spot edges extend away from the centre of the spot.

In FIG. 8 those elements which lie within a region of overlap of all four extended edges are identified by setting them to peak white on the T.V. display. The information could equally be used to specify addresses of the elements which lie within a black spot.

In order to achieve the sequence of operation described above, the applicant has devised a set of computer programs in accordance with the principles set forth above, which can take raw digitised T.V. pictures and process them to obtain indications of the positions of dark defects on white potatoes. The algorithm is general in that it can detect other types of feature in a picture with only slight modification.

The applicant also devised a system using similar general methods but embodied in hardware, which is suitable for real time use. An overall schematic diagram of the system is shown in FIG. 9. A video signal is produced by a camera 120 operating on a conventional raster scan system, converted to eight-bit digital form via analogue-to-digital converter 121, is received at an input 60 and is processed separately in respect of the two axes.

An edge detection unit, shown in more detail in FIG. 9(a), includes horizontal edge detection module 116, and a vertical edge detection module 118. The horizontal edge detection module 116 includes a delay unit 62 in which the input signal is delayed by a time representing one picture element, before being compared with the direct input in a subtraction unit 64. The difference signal may be positive or negative and is compared with a predetermined threshold level from computer-loaded threshold registers 66b, and 68b in a respective comparator 66a/66b. This results in a logic '1' output from comparator 66a at point 110 for a horizontal black-to-white transition and a logic '1' output from comparator 68a for a horizontal white-to-black transition.

In the vertical edge detector 118, the single element delay unit 62 of horizontal edge detector is replaced by a delay unit 70 in which the input signal is delayed by a time representing one line before being compared with the direct input in a subtraction unit 72. This can be done by reading the current signal into a 512 element×8 bit shift register, the data from which is read during a scanning of the subsequent line. Otherwise the vertical edge detection 118 is identical with horizontal edge detector 116. The difference signal is compared with a predetermined predetermined threshold level in a comparator 74a if positive or a comparator 76a if negative. A logic '1' output from comparator 74a represents a black-to-white vertical transition and an output logic '1' from comparator 76a represents a white-to-black vertical transition.

It will be appreciated that the horizontal edge detection unit, in comparing successive horizontal picture points, in fact will detect vertical edges in a T.V. picture as seen, and similarly the vertical edge detection unit will detect horizontal edges.

Figures 3B, 3C:
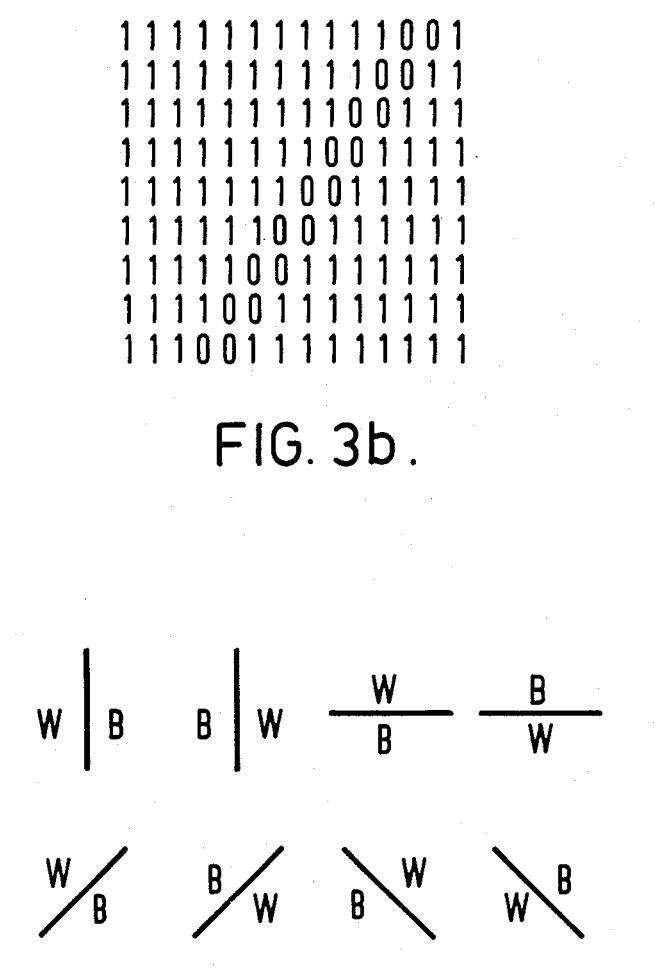

Thus the presence of one of the four types of horizontal and vertical transition illustrated in FIG. 3(c) is indicated by an output at a respective one of four output points 110, 111, 112, 113.

The pulses obtained at the four outputs 110 to 113 are synchronised by re-timing units 124 and 125, using an 11 MHz clock signal 116 and are then fed to horizontal edge expansion modules 126 and 127 and vertical edge expansion modules 128 and 129 respectively. AND gates 114 and 115 serve to "clean up" the wave form obtained. A single horizontal edge expansion module 126 is illustrated in FIG. 9(b), the other (127) being identical. The functioning of the module is as follows. When a logic '1' arrives from the re-timing unit via AND gate 114, a down-counter 80 is loaded with a constant from a computer-fed register 82 which controls the expansion distance. The counter 80 counts down at the system sample rate. While its outputs are greater than zero as detected by a digital comparator 84 the output at point 130 of the spreader module is at logic '1' indicative of the continued presence of an edge. When zero is reached the clock input to the counter 80 is inhibited via AND gate 86, and a logic '0' output at point 130 results until counter 80 is re-set by a new input from re-timing unit 125.

Vertical spreading module 128 and 129, are likewise identical with each other, one being illustrated on a larger scale in FIG. 10. The same principle (outlined in the flow chart of FIG. 4) is used, of pre-setting a counter, when an edge is detected, to the desired number of elements over which the spread is to extend, then decrementing the counter at element rate. The extended edge is thus present while the counter output is non-zero. Since vertically adjacent picture elements are displaced in time by one TV line period (64 micro seconds), and if there are taken to be 512 elements in the active part of a line, it is in principle necessary to provide 512 separate counters. This can be achieved in practice by holding the states of a notional bank of 512 counters in a 512 element recirculating shift register. FIG. 10 illustrates one hardware solution, which is capable of increasing the apparent height of a vertical edge to a maximum of 15 lines.

A 4-bit subtractor 90 receives two inputs A and B and outputs the difference (A−B) to a 4-bit 512 element shift register 92. Input A is received from a data selector 94 which responds to the presence of a signal at input 96 indicating the detection of a vertical edge by the circuit of FIG. 9(a). When that signal is present, selector 94 causes input A to be equal to the constant N which is derived from computer-loaded register 98 and indicates the number of picture elements over which the desired spread is to extend. In the absence of a current edge detection signal at the input 96, selector 94 switches the output from shift register 92 to provide input A. When the output from register 92 is non-zero, the desired spreading for the picture element concerned has not been completed. The value of input A is tested by an OR gate 100. When input A is greater than zero, the output from OR gate 100 is a logic '1' which appears at an output 132 as a spread instruction signal and also sets the value of input B. For input A=N, and therefore input B=1, the output from subtractor 90 is (N−1) which is loaded into register 92 on the next 11 MHz clock pulse to appear at an input 104. If the edge is present on one line only, the value (N−1) appears at input A after 512 clock periods, there being no new edge detection signal. The spread instruction again appears at output 132 and the decremented value (N−2) is entered in register 92. It will be clear that the process is repetitive until spreading over the desired N elements is completed.

Thus to summarise, a 4-bit subtractor 90 which calculates (A−B) takes as input A either the constant, N, indicating the desired spread, if an edge is detected by previously described hardware, or if not, the output from a 4-bit 512 element shift register. If input A to the subtractor 90 is greater than zero (detected by the OR gate 100) the least significant bit of input B is set to logic '1', the remaining bits being permanently zero. Thus, the counter output is (N−1), which is loaded into the shift register by the next 11 MHz clock pulse. Assuming the edge is present on one line only, after 512 clock periods, (N−1) appears at input A, and (N−2) at the output and so on. A '1' at the OR gate output for any picture element indicates that a vertical edge, either original or extended, has been detected.

When the count for a particular element falls to zero, the OR gate output goes to logic '0', and the subtractor output is also zero, a state that then persists until an edge is found. The outputs from the vertical edge detector modules appear at outputs 132 and 133, and these outputs, together with horizontal edge outputs 130 and 131 are synchronised by re-timing unit 140.

Because the above described system operates in real time, and comparisons with neighbouring picture points are effected only via time delays, the process of spreading a detected edge represents the labelling as edges of picture elements which are displaced from the element at which the data originated. Since the desire is to produce an indication of points which are labelled as boundary regions by each of the spreading modules 126 to 129, it is now necessary to bring the associated edges into register. This is carried out by means of signal delay modules 142, 144, 146, the effect of which is illustrated in FIG. 11. Different stages are shown in diagrams (a), (b), (c) and (d).

Figure 11D:
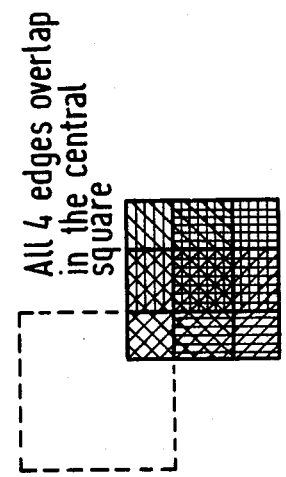
Figure 11C:
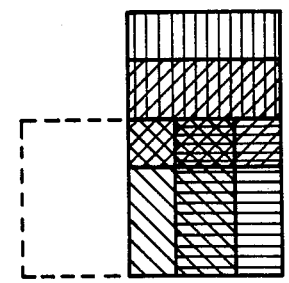
Figure 11A:
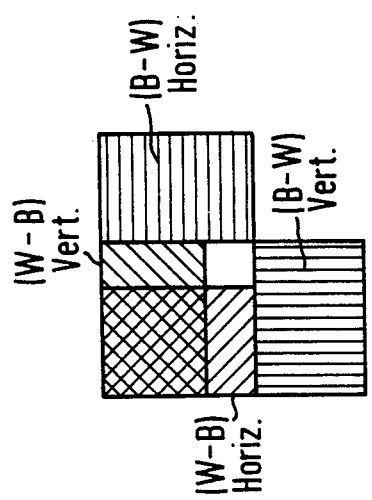
Figure 11B:
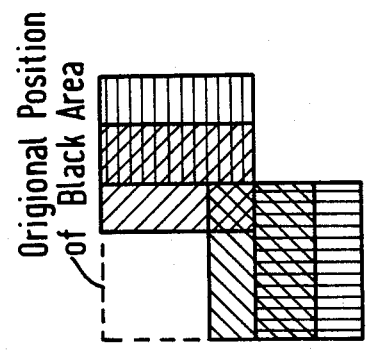

FIG. 11(a) shows the idealised spreader output for a rectangular black area on a white background (i.e. as would be obtained by direct combination of outputs 130 to 133). In delay module 144 the retimed output 131 corresponding to a white-to-black transition is delayed by delay unit 141 by an amount corresponding to the horizontal spreading distance. Similarly in delay module 142, a white-to-black vertical boundary is delayed by an amount corresponding to the vertical spreading distance. In each case the delayed signal is combined with the non-delayed signal for that direction by an AND gate 160, 161. The effect which would be achieved by the notional combination of the outputs at points 147 and 148 is illustrated in FIG. 11(b).

Further time delays to bring all four edges in to register are provided by delay module 146. Delay Unit 151 delays the combined horizontal edge signal 147 by an amount corresponding to the vertical spreading distance. The effect (i.e. the notional effect of the combination of output 149 of unit 151 and output 148 of AND gate 161 is illustrated in FIG. 11(c). Delay unit 154 delays the combined vertical edge signal 148 by an amount corresponding to the horizontal spreading distance to achieve the final result, as illustrated in FIG. 11(d). The centre of the detected black area is indicated by the region where all four components overlap. The position of the black area is shifted from the original but the original position may be simply derived from knowledge of the time delays.

Additionally, it is to be appreciated that the extent of the delays needed for registration need not be set equal to spreading distances. For example, if the delays are made greater than the spreading distances, the system can be made to discriminate against blemishes smaller than a certain size. In practice, all parameters are made capable of independent control.

Although in the foregoing description reference is made to difference signals between adjacent lines, because of the interlacing in the raster scan system, this represents alternate lives in the image as seen. It has been found furthermore that calculating differences between alternate rather than adjacent picture points in the horizontal direction gives rise to improved results.

As mentioned above one method of providing timing signals to provide an indication of position along the length of the roller table is to provide markings on the rollers for synchronisation of the raster scan.

In a preferred method, however, a timing signal is generated directly from the movement of the roller table. In a further preferred embodiment the spot detection system is arranged so as to operate only in the periods of the line scan corresponding to the same timing signal generated by movement of the roller bed referred to as the "roller function", may be used both to time this operation of the spot detection system, and to provide an indication of positions along the roller table. If displayed on a picture monitor, the roller function would appear as a series of horizontal stripes on the screen, the stripes lying over the roller gaps and tracking their motion. The information on roller position may be provided by a pair of toothed discs attached to the main roller drive shaft which produce electrical outputs via photoelectric sensors. The first disc gives one pulse per roller passage, the second sixteen.

The roller function itself is generated by a pair of 'down' counters, constituting a digital multivibrator. The counters are preset to the desired number of television scan lines for the active and inactive (mark and space) durations respectively.

The first counter is decremented once per TV line, and the active part of the roller function cycle is obtained while its outputs are non-zero. When its count reaches zero, the second counter is enabled and proceeds to decrement towards zero in the same way. When its outputs reach zero both counters are reloaded and the cycle repeats itself, hence the designation of the system as a 'digital multivibrator'.

The tracking action is obtained by delaying the start of the first counting cycle of the first counter by means of a third counter. This is loaded once per field from an accumulator. The accumulator is incremented by a preset amount by the 16 pulse/roller control signal, while it is reset to zero by the 1 pulse/roller component.

Since there are provided means for generating 16 pulses per roller, it is convenient if the number of television lines per roller pitch is an integral multiple of 16, say 3, giving 48. Thus, in the practical implementation of the defect detector the accumulator increment is 3, the 'active' part of the roller function cycle is 22 TV lines, while the inactive part is 48−22=26. As the active picture area used by the system contains approximately 287 lines per field, the number of roller pitches seen by the camera is adjusted to 287/48=5.979 or 6 in practice. This gives adequate coverage of the width of the roller table, since the actual roller pitch is 3.25 inches (8.25 cm), giving the distance along the table seen by the camera as 3.25×6=19.5 inches (49.5 cm). The television aspect ratio is 4:3, so the equivalent width seen is 19.5×4/3=26 inches (66 cm): the actual table width is 25 inches (63.5 cm).

An automatic selection system has been described with particular reference to the detection of black spots in potatoes but the possibility of application will be apparent in the detection either of flaws or of desirable features particularly features having fairly sharply defined boundaries in any context in which image analysis is desired. The term illumination has been used since in general visible light will be used but clearly the use of any other radiation such as infrared, ultra violet, radiation may be used.

Whilst it is generally advantageous to operate an automatic inspection system with a continuously moving conveyor the benefit of the defect analysis procedure may of course be obtained with a batch or stop-start means for presenting articles for selection. The image processing method and apparatus may be used for examining a single article, sheet material, or other form of substance, for examining paintwork or the like of articles such as automobile, or for any other purposes in which spot detection is desired.

I claim:

1. Apparatus for detecting a bounded region of an image, which apparatus comprises means for scanning the image via a raster scan to produce a signal indicative of image intensity at a plurality of picture points, means for comparing the image intensity at each of the said picture points with that of a neighbouring point in each of at least two directions to derive therefrom a difference value, means for labelling the picture points as corresponding to region boundaries whenever the difference values exceed a predetermined threshold value, means for expanding the region boundaries by labelling a number of further picture points as region boundaries such that boundaries between neighbouring picture elements along a scan line are unidirectionally expanded to successive neighbouring picture elements along the said scan line and boundaries between neighbouring picture elements of neighbouring scan lines are unidirectionally expanded to neighbouring successive scan lines, and means for time-shifting the signals associated with different types of expanded region boundaries by different amounts to superimpose the expanded boundaries for a region lying wholly within the bounded region of the image.

2. Apparatus as claimed in claim 1 wherein the comparing means includes a delay element for delaying a signal for a period corresponding to an integral number of picture points, and a subtractor for comparing the delayed signal with a non-delayed signal.

3. Apparatus as claimed in claim 1, wherein the comparing means is arranged to compare alternate points in the vertical and horizontal directions of the raster scan.

4. Apparatus as claimed in claim 1, wherein the means for expanding the region boundaries includes a register for holding the value of the desired spreading distance, and a counter for decrementing the value of the desired spreading distance over the desired number of picture points.

5. Apparatus as claimed in claim 1, wherein the time shifting means is arranged to delay the respective signals by an amount approximately corresponding to the time interval on the raster scan between the picture points over which the boundaries are expanded.

6. Apparatus as claimed in claim 1 wherein said number of further picture points is from 5 to 10.

7. Apparatus as claimed in claim 6 wherein said number of further picture points is 7.

8. Apparatus as claimed in claim 1 including means for selectively varying said number of further picture points by which the boundaries are expanded, and the period by which the said signal is delayed by the delay element.

9. Apparatus as claimed in claim 8 wherein said number of further picture points is from 5 to 10.

10. Apparatus as claimed in claim 9 wherein said number of further picture points is 7.

11. A method of detecting a bounded region of an image, which method comprises the steps of scanning the image via a raster scan to produce a signal indicative of image intensity at a plurality of picture points, comparing the image intensity at each of the said picture points with that of a neighbouring point in each of at least two directions to derive therefrom a difference value, labelling the picture points as corresponding to region boundaries whenever the difference values exceed a predetermined threshold value, expanding the region boundaries by labelling a number of further picture points such that boundaries between neighbouring picture elements along a scan line are unidirectionally expanded to successive neighbouring picture elements along the said scan line and boundaries between neighbouring picture elements of neighbouring scan lines are unidirectionally expanded to neighbouring successive scan lines time-shifting the signals associated with different types of expanded region boundaries by different amounts to superimpose the expanded boundaries for a region lying wholly within the bounded region of the image.

12. A method of detecting a flaw in an area of sheet material which method includes a method of detecting a bounded area as defined in claim 11.

13. Apparatus for detecting a bounded region of an image, which apparatus comprises:
scanning means for scanning the image and for producing a signal indicative of image intensity at a plurality of successive picture points;
deriving means for deriving difference values between neighbouring points in a plurality of directions to determine the presence of positive-going and negative-going region boundaries;
labelling means for labelling successive picture points according to whether or not they lie within a predetermined number of successive picture points in a specified direction from a region boundary and for expanding each of the said boundaries by the said predetermined number of picture points, said boundary expansion by said labelling means being such that both positive-going and negative-going parallel boundaries are expanded in the same direction;
time-shift means for applying time-shifts to the expanded boundaries, the time shift applied for a positive-going boundary being different from that applied for a negative-going boundary, to thereby superimpose the expanded boundaries for a region lying wholly within the bounded region of the image; and
means for generating an output in response to said superimposition of a plurality of the expanded boundaries.

14. Apparatus as claimed in claim 13 wherein the predetermined number of picture points is from 5 to 10.

15. Apparatus as claimed in claim 14 wherein the predetermined number of picture points is 7.

16. Apparatus as claimed in claim 13 including means for varying the predetermined number of picture points by which the boundaries are expanded, and the degree of time shift applied, to thereby vary the size of bounded region to be detected by the apparatus.

17. Article sorting apparatus comprising:
conveying means for conveying through an inspection region articles having predominantly a first value of surface reflectivity but bearing occasional surface features having a second value of reflectivity which is substantially different from the first value;
means for illuminating each article in the inspection region;
sensing means responsive to radiation reflected from the article for scanning the inspection region to derive an image signal and for processing the derived image signal, said sensing means including:
(a) scanning means for scanning the image to produce a signal indicative of image intensity at a plurality of successive picture points;
(b) means for deriving difference values between neighboring points in a plurality of directions to determine the presence of positive-going and negative-going region boundaries;
(c) means for labelling successive picture points on the scan according to whether or not they lie within a predetermined number of successive picture points in a specified direction from a region boundary to thereby extend each of the said boundaries by the said predetermined number of picture points, said boundary extension being such that both positive-going and negative-going parallel boundaries are extended in the same direction; and
(d) time-shift means for applying time-shifts to the extended boundaries, the time-shift applied for a positive-going boundary being different from that applied for a negative-going boundary, to thereby superimpose the extended boundaries for a region lying wholly within the bounded region of the image thereby to generate an output signal;

said article sorting apparatus further comprising deflection means responsive to the said output signal to cause the article bearing such feature to be routed differently from the other articles.

18. Apparatus as claimed in claim 17 for sorting rounded articles such as potatoes, wherein the conveying means comprises a roller table formed of a plurality of rotatable rollers, connected together for rotation and translational movement in the inspection area.

19. Apparatus as claimed in claim 17 wherein the deflector means comprises an array of deflector devices arranged across the path of the conveyor means downstream of the inspection area, and drive means for driving selected deflector devices, the selection of deflector devices actuated being controlled in dependence upon a first coordinate of a location in the scanned area and the timing of operation of the deflector devices being controlled in dependence upon a second coordinate of a location in the scanned area.

* * * * *